(12) United States Patent
Weston et al.

(10) Patent No.: US 8,282,609 B2
(45) Date of Patent: Oct. 9, 2012

(54) SAFETY NEEDLE

(75) Inventors: Terence Edward Weston, Swannington (GB); Douglas Arthur Emmott, Ipswich (GB)

(73) Assignee: Salvus Technology Limited, Stradbroke, Suffolk (GB)

( * ) Notice: Subject to any disclaimer, the term of this patent is extended or adjusted under 35 U.S.C. 154(b) by 1172 days.

(21) Appl. No.: 10/545,160

(22) PCT Filed: Feb. 9, 2004

(86) PCT No.: PCT/GB2004/000516
§ 371 (c)(1),
(2), (4) Date: Aug. 11, 2005

(87) PCT Pub. No.: WO2004/071560
PCT Pub. Date: Aug. 26, 2004

(65) Prior Publication Data
US 2006/0167411 A1    Jul. 27, 2006

(30) Foreign Application Priority Data

Feb. 11, 2003  (GB) .................................. 0303026.9
Apr. 7, 2003   (EP) .................................. 03252192
Nov. 27, 2003  (GB) .................................. 0327602.9

(51) Int. Cl.
*A61M 5/00*  (2006.01)
*A61M 5/32*  (2006.01)

(52) U.S. Cl. .......................... 604/263; 604/198; 604/192

(58) Field of Classification Search .................. 604/263, 604/111, 110, 192–194
See application file for complete search history.

(56) References Cited

U.S. PATENT DOCUMENTS

| | | | |
|---|---|---|---|
| 1,845,036 A | 2/1932 | Busher |
| 3,114,455 A | 12/1963 | Claisse et al. |
| 3,134,380 A | 5/1964 | Armao |
| 3,677,245 A | 7/1972 | Welch |
| 4,553,541 A | 11/1985 | Burns |
| 4,795,432 A | 1/1989 | Karczmer |

(Continued)

FOREIGN PATENT DOCUMENTS

CN   1777453 A   5/2006

(Continued)

OTHER PUBLICATIONS

United States Patent and Trademark Office Action mailed Oct. 1, 2008.

(Continued)

*Primary Examiner* — Nicholas Lucchesi
*Assistant Examiner* — Pritesh Patel
(74) *Attorney, Agent, or Firm* — Panitch Schwarze Belisario & Nadel LLP (57) ABSTRACT

This invention relates to an accessory for attaching to a needle to prevent needle stick injuries. The safety needle accessory is suitable for use with a hollow needle and comprises a needle hub surrounding the needle and a slidable sleeve slidably mounted on the needle hub. The slidable sleeve bears resiliently on the needle hub such that, in use, as the slidable sleeve is caused to move into a retracted position. A restoring force is generated within the slidable sleeve and on removal of the needle from the patient the restoring force causes the slidable sleeve to move into an extended position covering the needle tip. The safety needle locks in this position after removal of the needle from the patient.

34 Claims, 8 Drawing Sheets

U.S. PATENT DOCUMENTS

| | | | |
|---|---|---|---|
| 4,813,940 | A | 3/1989 | Parry |
| 4,850,996 | A | 7/1989 | Cree |
| 4,911,693 | A | 3/1990 | Paris |
| 4,927,019 | A | 5/1990 | Smedley et al. |
| 5,015,240 | A | 5/1991 | Soproni et al. |
| 5,104,384 | A | 4/1992 | Parry |
| 5,219,339 | A | 6/1993 | Saito |
| 5,242,401 | A | 9/1993 | Colsky |
| 5,312,366 | A | 5/1994 | Vailancourt |
| 5,336,197 | A | 8/1994 | Kuracina et al. |
| 5,385,561 | A | 1/1995 | Cerny |
| 5,421,347 | A | 6/1995 | Enstrom |
| 5,549,568 | A * | 8/1996 | Shields .................. 604/192 |
| 5,601,535 | A | 2/1997 | Byrne et al. |
| 5,658,256 | A | 8/1997 | Shields |
| 5,669,888 | A | 9/1997 | Trapp |
| 5,755,696 | A | 5/1998 | Caizza |
| 5,891,103 | A | 4/1999 | Burns |
| 5,910,130 | A | 6/1999 | Caizza et al. |
| 5,944,699 | A | 8/1999 | Barrelle et al. |
| 5,971,966 | A | 10/1999 | Lav |
| 6,203,529 | B1 | 3/2001 | Gabriel et al. |
| 6,210,374 | B1 | 4/2001 | Malencheck |
| 6,261,264 | B1 | 7/2001 | Tamaro |
| 6,331,174 | B1 | 12/2001 | Spaliek et al. |
| 6,398,762 | B1 | 6/2002 | Otto et al. |
| 6,511,460 | B1 | 1/2003 | Arnissolle |
| 6,537,259 | B1 | 3/2003 | Niermann |
| 6,685,676 | B2 | 2/2004 | Jansen et al. |
| 7,041,086 | B2 * | 5/2006 | Yang .......................... 604/198 |
| 7,182,734 | B2 | 2/2007 | Saulenas et al. |
| 7,223,258 | B2 | 5/2007 | Crawford |
| 2002/0004648 | A1 | 1/2002 | Larsen et al. |
| 2002/0087180 | A1 | 7/2002 | Searle et al. |
| 2003/0014018 | A1 | 1/2003 | Giambattista et al. |
| 2003/0144633 | A1 | 7/2003 | Kirchhofer |
| 2004/0116877 | A1 | 6/2004 | Yang |
| 2004/0210196 | A1 | 10/2004 | Bush, Jr. et al. |
| 2005/0038391 | A1 | 2/2005 | Wittland et al. |
| 2006/0129173 | A1 | 6/2006 | Wilkinson |
| 2006/0167411 | A1 | 7/2006 | Weston et al. |
| 2008/0183140 | A1 | 7/2008 | Paproski et al. |

FOREIGN PATENT DOCUMENTS

| | | |
|---|---|---|
| EP | 0467173 | 1/1992 |
| EP | 0744183 A2 | 11/1996 |
| EP | 0815884 A1 | 1/1998 |
| EP | 1252907 | 10/2002 |
| EP | 1447108 A1 | 8/2004 |
| EP | 1535640 A | 6/2005 |
| EP | 1558311 | 8/2005 |
| FR | 2701848 A1 | 2/1993 |
| JP | 3158171 A | 7/1991 |
| WO | 91/11212 A | 8/1991 |
| WO | WO 91/11212 A1 | 8/1991 |
| WO | 9400172 A1 | 1/1994 |
| WO | 9419036 A1 | 9/1994 |
| WO | 01/76665 A | 10/2001 |
| WO | WO 01/76665 A1 | 10/2001 |
| WO | 01/91837 | 12/2001 |
| WO | 02/089878 A | 11/2002 |
| WO | 02/100467 A | 12/2002 |
| WO | 03/066141 | 8/2003 |
| WO | 2004/000397 A | 12/2003 |
| WO | 2004/0171560 A | 8/2004 |
| WO | 2004069302 A2 | 8/2004 |
| WO | WO2004071560 A1 | 8/2004 |
| WO | 2006082350 A1 | 8/2006 |
| WO | W02006090118 A1 | 8/2006 |
| WO | 2008067467 A2 | 6/2008 |

OTHER PUBLICATIONS

Examination Report in related Australian Application No. 2004212245 dated Nov. 11, 2008.
First Chinese Office Action for the related Chinese Patent Application No. 2004800069251; dated Dec. 28, 2007; English translation only (5 pages).
Second Chinese Office Action for the related Chinese Patent Application No. 200480006925.1; dated Feb. 20, 2009; English translation only (3 pages).
Office Action for the related U.S. Appl. No. 11/815,475 issued Apr. 9, 2009.
Office Action for the related U.S. Appl. No. 11/815,475 issued Aug. 21, 2009.
European Search Report for the related European Patent Application No. 03 25 2192, dated May 26, 2003; 4 pages.
Office Action for the related Japanese Patent Application No. 2006-502257 issued Sep. 11, 2009.
Office Action for the related Chinese Patent Application No. 200580047707.7 issued Sep. 25, 2009.
Written Opinion for the related International Patent Application No. PCT/GB2004/000516 issued May 27, 2004.
Chinese Office Action for the related Chinese Patent Application No. 200680006138.6; dated Jun. 5, 2009; 8 pages (including English translation).
Office Action for the related U.S. Appl. No. 11/817,075 issued Dec. 21, 2009.
Office Action for the related U.S. Appl. No. 11/815,475 issued Jan. 4, 2010.
International Search Report and Written Opinion for the related International Patent Application No. PCT/GB06/00528, dated May 22, 2006.
Chinese Office Action for the related Chinese Patent Application No. 200680006138.6; dated Dec. 11, 2009 (English translation only).
Third Chinese Office Action for the corresponding Chinese Patent Application No. 200480006925.1; dated Jul. 10, 2009; English translation only (3 pages).
Japanese Office Action for the related Japanese Application No. 2006-502257 mailed Jan. 15, 2010.
Office Action for the related U.S. Appl. No. 11/817,075 dated Aug. 27, 2008.
Office Action for the related U.S. Appl. No. 11/817,075 dated Feb. 20, 2009.
Office Action for the related U.S. Appl. No. 11/817,075 dated Jul. 28, 2009.
International Search Report for the related International Application No. PCT/US2008/077352 mailed Jan. 30, 2009.
Partial European Search Report for the related European Application No. 09175295.6 dated Apr. 9, 2010.
Chinese Office Action for the related Chinese Application No. 200680006138.6 dated Apr. 15, 2010.
International Preliminary Report on Patentability for the related International Application No. PCT/US2008/077352 dated Apr. 13, 2010.
Office Action issued Dec. 7, 2010 in U.S. Appl. No. 12/470,220.
Office Action Issued Apr. 29, 2011 in U.S. Appl. No. 12/276,679.
Office Action Issued May 6, 2011 in U.S. Appl. No. 12/470,220.
Office Action issued Apr. 26, 2011 in JP Application No. 2007-556647.
Office Action issued Jun. 17, 2011 in U.S. Appl. No. 12/680,811.
Office Action Issued Sep. 7, 2010 in Japanese Application No. 2007-553675.
European Search Report issued on Oct. 4, 2010 in European Patent Application No. EP 09 17 5295.
Office Action issued Jul. 30, 2010 in Chinese Application No. 20068006138.6.
Office Action issued Dec. 23, 2011 in U.S. Appl. No. 12/276,679.
Office Action issued Jan. 5, 2012 in U.S. Appl. No. 12/680,811.
Witness statement of T. E. Weston (inventor), Aug. 27, 2010.
Second witness statement of T. E. Weston (inventor), Mar. 24, 2011.
Third witness statement of T. E. Weston (inventor), Jan. 5, 2012.
Witness statement of John Davison, May 3, 2011.
Statement from claimant in UK revocation proceeding regarding EP Patent No. 1558311, Jul. 15, 2010.
Defendant's counter-statement in UK revocation proceeding regarding EP Patent No. 1558311, Aug. 31, 2010.
Defendant's supplementary counter-statement in Uk revocation proceeding regarding EP Patent No. 1558311, Mar. 25, 2011.
Written Preliminary Evaluation in UK revocation proceeding regarding EP Patent No. 1558311, Nov. 10, 2011.

Witness statement of Barry Peter Liversidge on behalf of tip-top.com Ltd. in UK revocation proceeding regarding EP Patent No. 1558311, Jan. 19, 2012.

Defendant's further counter-statement in UK revocation proceeding regarding EP Patent No. 1558311, Jan. 17, 2012.

Defendant's consolidated counter-statement in UK revocation proceeding regarding EP Patent No. 1558311, Mar. 9, 2012.

Office Action issued Sep. 23, 2011 in CN Application No. 200880110889.1.

Office Action issued Nov. 18, 2011 in U.S. Appl. No. 11/817,075.

Office Action issued Jul. 29, 2011 in U.S. Appl. No. 11/817,075.

Definition of "seal" as found on Merriam-Webster.com, retrieved Jul. 21, 2011.

* cited by examiner

SAFETY NEEDLE

This application is a filing under 37 CFR 371 of PCT/GB2004/000516, filed Feb. 9, 2004, and claims priority from GB 0303026.9, filed Feb. 11, 2003, EP 03252192.4, filed Apr. 7, 2003 and GB 0327602.9, filed Nov. 27, 2003.

Needle stick injuries carry a significant risk of spreading infection, such as HIV and hepatitis, and are commonplace among healthcare workers. The USA has led the way in introducing legislation that obliges healthcare providers to use the safest devices when giving injections, intravenous drug administration and similar invasive procedures. Other countries are following and, even without legislation, the ever-present risk of litigation has alerted pharmaceutical companies and health authorities to seek suitable safe devices.

As a result of the heightened awareness of needle stick injuries, there have been a large number of inventions purporting to address this issue. Most take the form of a protective sleeve which covers the needle tip after the injection has been given, or means for retracting the needle rapidly into the syringe barrel. In the former case, a weakness of the designs has been the need for the user (i.e. the clinician) to perform an action to render the needle safe; thus if the step is omitted, the risk remains. Such a safety needle is exemplified by U.S. Pat. No. 4,911,693. In the latter case, the needle retraction mechanism requires that the syringe plunger is pushed to the end of its stroke in order to activate the retraction mechanism. In other words, virtually none of the devices are "fail safe". In many real-life situations, the patient can involuntarily react to the pain of the injection and pull away from the needle, exposing the sharp tip, and therefore presenting a risk of a needle stick.

Another drawback of prior art safety needles (which in the present context includes safety syringes) is that they are not compatible with current accepted practice. The problems includes drug incompatibility with the device construction materials, difficulty in using standard sterilising methods, difficulty in fitting to the syringe, large size, difficulty in filling, and very high cost.

Again, a common requirement for drug administration is to draw the drug from a vial or bulk container, or first reconstitute a lyophilised drug, and then draw up the required volume of drug from the reconstitution vessel. Good practice demands that separate needles are used for such procedures, and from a practical viewpoint, the needle used to draw up the drug usually will be larger than the delivery needle. Most of the prior art devices do not address this aspect.

Another common requirement is for pre-filled syringes, and for reasons of drug compatibility and long-term storage, the syringe barrel is often made from glass, with the hypodermic needle bonded into the delivery end of the syringe barrel. Alternatively, a few drugs are compatible with plastics, and there are available plastic syringe barrels with moulded or bonded-in hypodermic needles.

Some safety devices have addressed the problems associated with manually operated safety sleeves, such as the devices disclosed in. U.S. Pat. Nos. 4,813,940 and 5,104,384. High cost has, however, tended to be a significant deterrent which has resulted in poor commercial success of the better devices. Potential specifiers and purchasers are put off by the high cost (several times that of a basic syringe), and have been able to cite the fallibility of the devices which are available as a way of avoiding buying them.

Again, there is a huge "inertia" in the world's healthcare system. The massive investment in manufacturing plants, aseptic production and assembly, sterilisation, existing long-term supply contracts, the bewildering number of so-called safety syringes on offer, and the drawbacks already noted, have mitigated against rapid adoption of safety needles and syringes.

There is therefore still a need for a low cost safety needle which prevents needle stick injuries in healthcare workers.

According to the invention, there is provided a safety needle attachment for surrounding a needle having a longitudinal axis, comprising:
  a hub;
  a sleeve surrounding the hub and slidable relatively to hub in the axial direction;
  wherein the sleeve has a radially elastically deformable portion, and the hub has a radially converging or diverging portion,
  and wherein the sleeve is slidable in a first axial direction between a first position for fully or substantially fully surrounding the needle with the sleeve, and a second position for exposing the needle, wherein sliding between the first and second positions causes elastic radial deformation of the expandable portion engaging with the converging or diverging portion, and wherein the sleeve is further slidable in a second, opposite, axial direction between the second position and a third position for fully surrounding the needle by the sleeve, the force for sliding between the second and third positions being provided by the stored elastic energy in the radially deformable portion.

This arrangement uses radial elastic deformation of a part of the sleeve to provide the return force for the sleeve. This avoids the need for a separate spring, and can enable the device to have a three-piece construction (hub, needle and sleeve). This dramatically reduces the manufacturing cost and complexity of the device when compared with prior art devices.

Preferably, a portion of the sleeve is elastically deformable radially outwardly as it rides over a radially diverging portion of the hub.

A latching arrangement can engage when the sleeve reaches the third position to prevent subsequent movement of the sleeve in the first axial direction.

An intermediate position mat be provided between the first and second positions of the sleeve, in which the sleeve is retained in position. The injection end of the needle can project partially from the sleeve in the intermediate position, so that alignment of the injection is facilitated.

The third position of the sleeve can be the same axially as the first position. In this case, wherein movement of the sleeve in the first axial direction causes rotation of the sleeve about the longitudinal axis. This then allows the sleeve to return to a different angular position to the starting position, so that an angularly positioned locking arrangement can be engaged.

In one embodiment, the radially converging or diverging portion of the hub comprises at least one recess for engaging with the deformable portion of the sleeve in a starting position of the sleeve, and otherwise has a substantially smooth outer surface.

This arrangement enables the sleeve to be held (axially and angularly) in the starting position, but once released the sleeve can rotate during the injection. This provides resistance to damage when subjected to external forces. Also, lateral forces are kept to a minimum.

The smooth outer surface can be conical, or polygonal in cross section perpendicular to the longitudinal axis. Thus "smooth" in intended to cover angled edges but with internal angles less than 180 degrees, so that the sleeve can ride over the edges rather than being trapped by them. The polygon may also have curved sides.

The starting position of the sleeve can cause the needle to project from the sleeve, and the attachment then preferably further comprises a cap.

In another version, tracks are used, and the radially converging or diverging portion of the hub comprises at least one track running the length of the hub, and a branch is provided to the track which defines a recess for engaging with the deformable portion of the sleeve in a starting position of the sleeve.

Again, the starting position of the sleeve can cause the needle to project from the sleeve, and the attachment then further comprises a cap.

The deformable portion of the sleeve preferably comprises a plurality of circumferentially spaced tines. There may be four such tines, by way of example.

The present invention also provides a safety needle, an injection device and a syringe incorporating the safety needle attachment as defined above. The safety needle comprises a hollow needle and the safety needle accessory as defined above, and the syringe comprises a piston, a barrel and the safety needle as defined above The present invention further provides a method for injecting a patient using the safety needle as defined above.

The present invention will now be described with reference to the following drawings, in which.

In the drawings, like parts are given the same reference numerals.

The standard construction of a needle comprises a plastic needle hub which is tightly formed onto the needle (by moulding, gluing or thermal upsetting). The needle is protected by a plastic slidable sleeve which fits firmly but removably onto the needle hub. Normally the needle is packed in a pouch and the whole is sterilised, usually by gamma irradiation. Thus the typical needle comprises three parts, namely a hollow needle, a needle hub, and a removable sleeve.

The present invention may be conceptualised by comparing it with a conventional hypodermic needle: the component replacing the normal needle hub is one half of a returning mechanism, and the part that would be the protective slidable sleeve forms the other half of the mechanism, whilst also protecting the needle. Together with the needle, the component count is three, exactly the same as for a conventional hypodermic needle, and therefore a similar low manufacturing cost is achieved. Furthermore, the user does not have to learn a new technique, and so the adoption of the safety needle will not require special training of healthcare workers.

Figure 1:
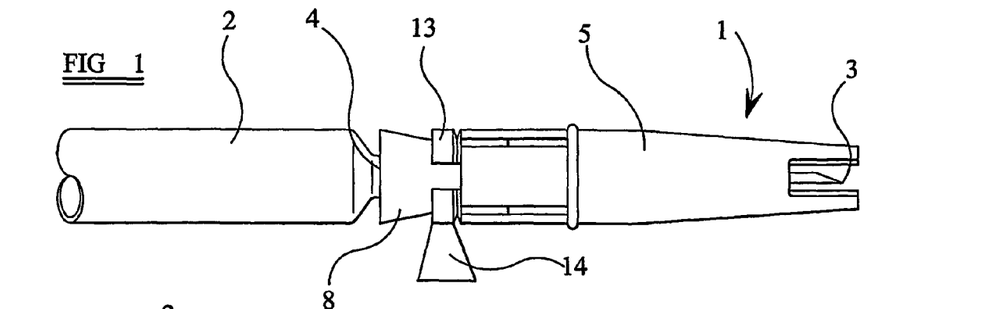
FIG. 1 shows a safety needle accessory of the present invention attached to a syringe.
Figure 2:
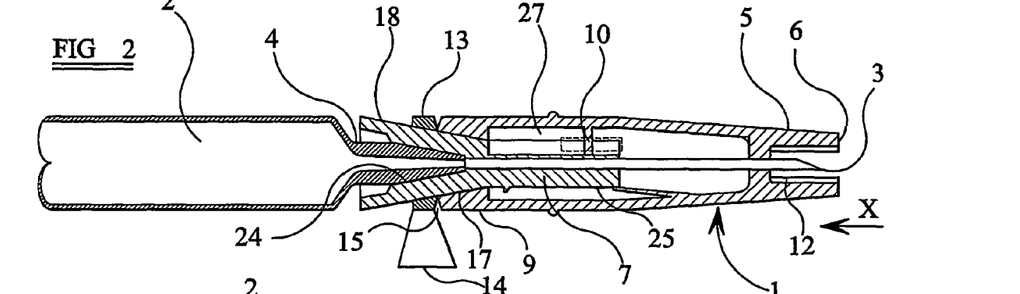
FIG. 2 shows a centre line cross-section through the safety needle accessory of FIG. 1 attached to a syringe.

FIG. 1 shows a first example, of safety needle 1 (i.e. the safety needle accessory and the needle 3) of the present invention as fitted to a male Luer taper connector 4 of a syringe 2, with the end of the hollow (e.g. hypodermic) needle 3 enclosed by the slidable sleeve 5. The slidable sleeve 5 is initially prevented from longitudinal movement on the needle hub 7 by a locking ring 13, which may be removed by pulling on the tab 14. The removable locking ring may be connected to the needle hub and/or the slidable sleeve. Although embodied in the Figures as cylindrical, the cylindrical shape of the needle hub and slidable sleeve may be replaced by triangular, rectangular or other shapes to suit the application;

FIG. 2 is a cross-section through the longitudinal axis of the safety needle 1. The needle hub 7 is cylindrical and terminates at the end which receives the syringe with a conical section 18, and is moulded onto the needle 3. The conical section 18 has an inner female Luer cone 24 which is shown frictionally attached to the male Luer cone 4 of syringe 2 (the Luer system for attaching the needle to the syringe has two main forms, that is a taper friction fit and a screw thread and both are possible in the present invention).

Figure 3:
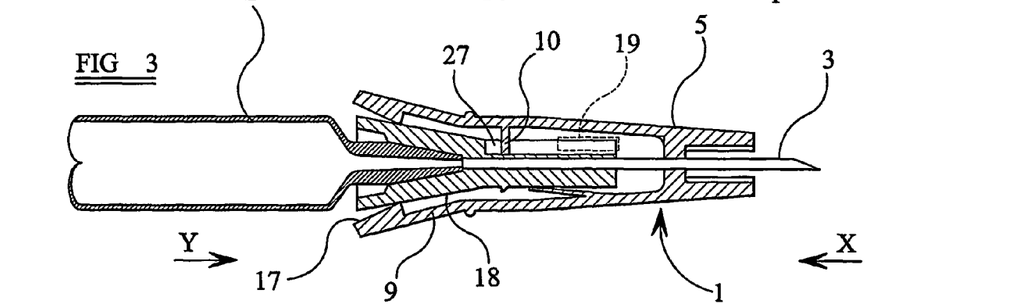
FIG. 3 shows the slidable sleeve partly retracted to expose the hollow needle.

The cylindrical slidable sleeve 5 shrouds the needle 3 and the needle hub 7, and is freely sliding on and guided by the needle hub 7. At the receiving end (i.e. the syringe end) of slidable sleeve 5, there are four cantilever arms 9 which bear resiliently upon the surface of the conical section 18. The slidable sleeve 5 is free to slide on the needle hub 7, but is temporarily prevented from doing so by the locking ring 13. Locking ring 13 is moulded integrally with the slidable sleeve 5 by a frangible joint 15, and may be partially or wholly detached by pulling on the tab 14 to break the frangible joint 15. It is preferred that the ring 13 remains attached to the slidable sleeve 5 to reduce the number of discarded parts. In addition, the frangible joint provides a tamper-evident lock. Alternatively, the locking ring 13 may be moulded to the needle hub 7 via a suitable frangible connection. When the locking ring 15 is removed, as shown in FIG. 3, the slidable sleeve 5 may be pushed in the direction of arrow X by acting on the face 6, when it will move relative to the needle hub 7 to expose the needle 3. As the slidable sleeve 5 moves, the cantilever arms 9 are forced outwards by the surface of the conical section 18. The cantilever arms 9 are deform radially outwardly elastically, and the reaction force against the surface 18 produces a resultant force Y (FIG. 3) acting against arrow X, so that when the original force is removed, the slidable sleeve 5 returns to cover the tip of needle 3. Since the restoring force is provided by the slidable sleeve 5 itself, no separate spring, e.g. a helical spring, is required.

Figure 6:
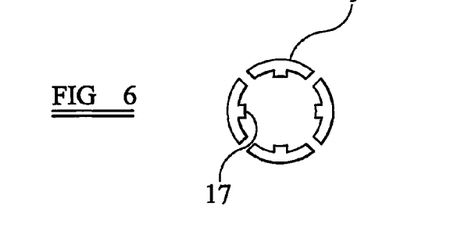
FIG. 6 shows the receiving end of the slidable sleeve showing the cantilever arms.

As shown in FIG. 6, the cantilever arms 9 may have pads 17 which bear onto the surface 18 and, by suitably designing the bearing surfaces of the pads 17, various spring characteristics may be obtained. Although four cantilever arms 9 are shown, any number could be employed. At least one cantilever arm 9 is required for this embodiment although 2 to 6 are preferred and particularly preferably four.

Figure 8:
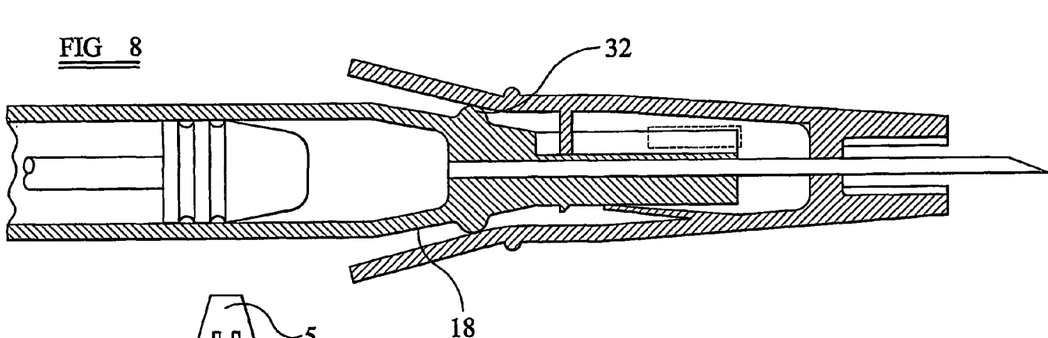
FIG. 8 shows a second modified version of the accessory of the invention having an integral syringe barrel and needle hub.

Although the surface 18 is exemplified by a conical surface, other embodiments may be used within the scope of the present invention. In the Figures the surface is straight, i.e. substantially conical (namely sufficiently conical to generate a restoring force). However, the surface need not be straight as shown, but may be curved to give a more linear return rate. Thus the force Y could be substantially constant over a reasonable working stroke of the slidable sleeve 5. In addition, the whole surface 18 of the receiving end of the needle hub 17 need not be conical. In fact just one tapered section, e.g. a tapered ridge, would be sufficient. The tapered section does not have to project from the surface of the needle hub 7. The tapered section could also descend into the wall of the needle hub, i.e. a tapered detent rather than a tapered ridge. Also, as described below with reference to FIG. 8, provided the slidable sleeve 5 is suitably configured, a projection in the surface 18 of the needle hub 7 will suffice.

These different arrangements provide a great deal of design flexibility in the safety needle accessory of the present invention. For example, the linearity of the return rate may be varied depending on the particular requirements for a particular application.

The way the sleeve is retracted and then returns to a safe position has been described above. A mechanism is also preferably provided for locking the sleeve in the safe position, and this mechanism is described with reference to FIG. 4.

Figure 4:
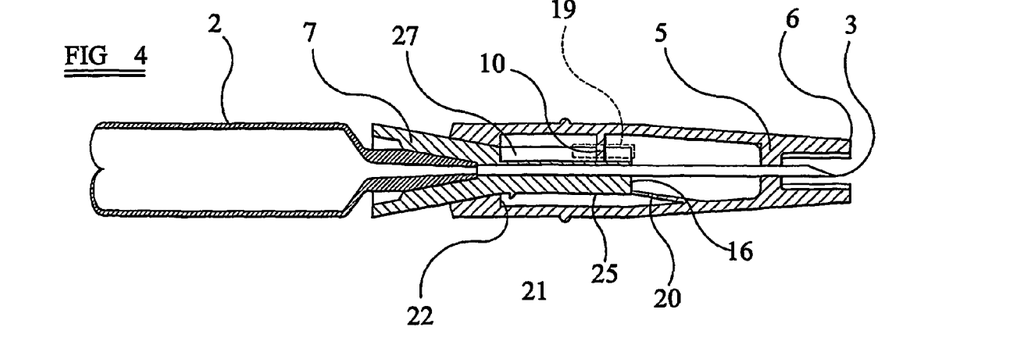
FIG. 4 shows the safety needle accessory with the slidable sleeve in an extended and locked position.

When the slidable sleeve 5 returns in direction Y, it travels slightly past its original staring position, so that a resilient pawl 20 shown in FIG. 4, which was depressed by the outer surface 25 of hub 7, snaps out to act against a face 16 of the hub 7. This ensures that the slidable sleeve 5 cannot be pushed back towards the syringe 2, and therefore the needle 3 is safely covered; It is preferred that there is a pre-load between the cantilever arms 9 and hub 7 to ensure that the slidable sleeve 5 is sufficiently biased in the direction of arrow Y to complete its full displacement potential.

In this design, there are therefore three operative positions of the sleeve—the starting position, the injection position and the safety position.

In the starting position (a first extended position), the slidable sleeve is able to be moved towards the receiving end of the needle hub and in the safety position (a second extended position) the slidable sleeve is in a locked position.

Figure 5:
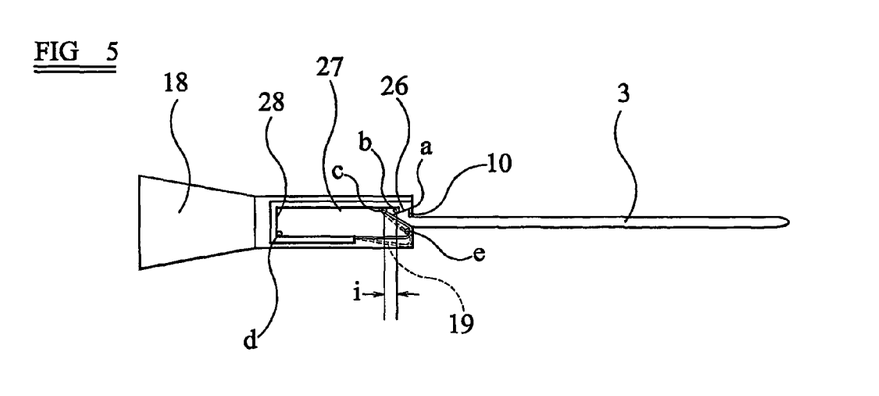
FIG. 5 shows an example of detent mechanism.

The different start and finish positions of the slidable sleeve 5 are determined by a detent mechanism shown in FIG. 5, which is to be read in conjunction with FIGS. 2, 3 and 4.

FIG. 5 shows schematically one way in which a coupling between the sleeve 5 and the hub 7 may function. This coupling is shown even more schematically in FIGS. 3 and 4 as reference 19.

The sleeve has a pin 10 projecting from an inner surface of the sleeve housing and this projects into a chamber within the hub 7.

The coupling is arranged so that after the first two or three millimeters of movement of the sleeve, the pin 10 triggers a switching operation by tripping a latching pawl, so that the slidable sleeve returns only to the safety position.

In the initial assembly of the safety needle, the slidable sleeve 5 is placed over the needle 3 with pin 10 proximate to a tab 26 formed as part of the needle hub 7 at position a. As the slidable sleeve 5 is moved further, the pin 10 deflects a resilient pawl 19, until the pin 10 is trapped behind tab 26 at position b. In this position, the slidable sleeve 5 is trapped on the needle hub 7 and cannot be removed without applying considerable force. This is the position of the components as supplied to the end user, and the location of the locking ring 13 takes account of this.

With the locking ring 13 removed, the slidable sleeve 5 is pushed further towards the syringe 2, and pin 10 again deflects the resilient pawl 19 until the pin 10 reaches position c. This distance i defines the initial displacement of the slidable sleeve 5, when starting the injection, and the tip of needle 3 may be level with the face 6 of slidable sleeve 5. The slidable sleeve 5 may now be moved towards the syringe until the pin 10 reaches the end wall 28 of the chamber 27 at position d. This position defines the maximum displacement of slidable sleeve 5, and thus the maximum exposure of the needle 3.

At any time, if the force acting on slidable sleeve 5 is removed, the slidable sleeve 5 will return in the direction of arrow Y until pin 10 reaches the position e. This is the safety position, and has the sleeve slightly further extended than in the starting position (b). Pin 10 would also help, prevent the removal of slidable sleeve 5, but additionally a tooth 21 on the outside of the hub 7 is now proximate to an internal face 22 on a cantilever arm 9, which prevents the removal of the slidable sleeve 5.

In this final position, a pawl 20 on the inside surface of the sleeve 5 engages with end face 16 of the hub 7 and prevents the slidable sleeve 5 from being moved. It should be noted that with the present diagrammatic presentation of the safety needle, a small amount of rotational movement is necessary between the slidable sleeve 5 and hub 7 to permit the pin 10 to move from position c to position e, but the rotation is preferably negligible.

The tab 26, resilient pawl 19, and chamber 27 are moulded integrally with the needle hub 7, and the pin 10 extends into the chamber and is allowed to move freely except where controlled by the detent and the boundaries of the chamber.

The detent mechanism is interchangeable between the slidable sleeve 5 and needle hub 7 if required. Also, the detent mechanism described hereinabove is but one of a number of such mechanisms, the main requirement being to permit the following sequence of operation: permit the slidable sleeve to be moved sufficiently so that the opening in the slidable sleeve is level with or just in front of the needle tip, at which position the detent must be activated so that if the displacing force on the slidable sleeve is removed, the slidable sleeve slides forward and locks, thus protecting the user from contact with the needle tip. Typically, the tip of the needle would be about 3 mm back from the face of the opening in the slidable sleeve at the start, and 1 mm back from the face when the detent is activated.

Figure 7:
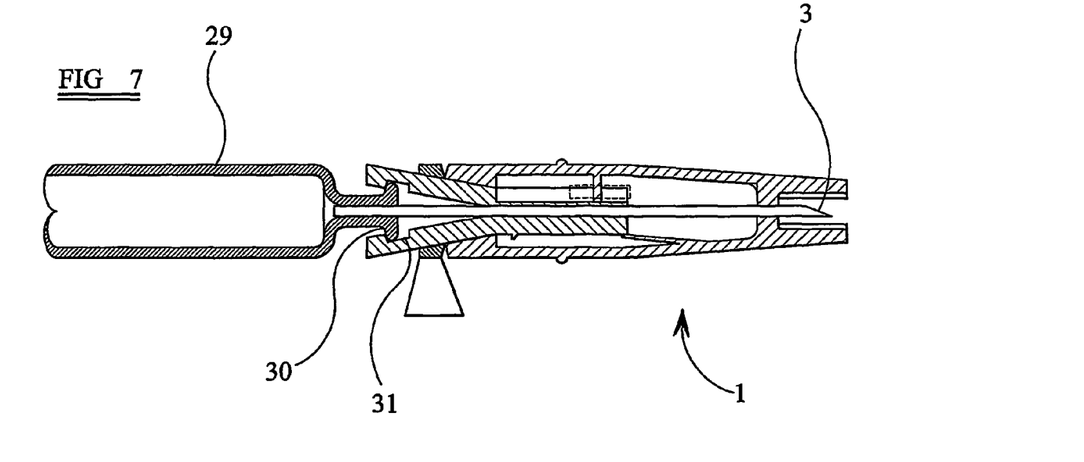
FIG. 7 shows the barrel of a typical glass syringe used commonly for pre-filling with a drug, assembled with a first modified version of the safety needle accessory of the present invention.

As an alternative to being supplied pre-assembled, the safety needle accessory may be supplied without a needle and then the accessory is attached to an injection device having an integral needle. FIG. 7 shows the device 1 as previously described, except that in this embodiment the needle 3 is bonded into the outlet end of the syringe barrel 29. The needle is free to pass through the needle hub 7, and the conical part of the hub is adapted at 31 to snap-fit over the projection 30.

The form of projection 30 is produced as a result of rolling the glass onto a mandrel, whereby the excess glass is forced in to the shape as shown.

Alternatively, a more defined snap-fitting termination may be formed, the object being to make the device 1 difficult to remove after assembling it to the syringe barrel.

FIG. 8 shows a safety needle 1 in which the needle hub 7 is integral with the barrel of the syringe 2. That is, the injection end of the barrel of the syringe, or similarly any other injection device, has an outer surface which is adapted to deflect the slidable sleeve 5 thereby generating the restoring force. The slidable sleeve 5 is simply placed on to the needle hub and then the safety needle is used as described herein. The material of the needle hub 7, which also constitutes the barrel of the syringe, would, of course, have to be made from a drug-compatible material. Suitable drug-compatible materials include glass and multilayer plastics materials having an outer rigid layer and an inner drug compatible layer. An advantage of having an integral needle hub 7 and barrel is that the number of component parts and hence the cost is further reduced.

FIG. 8 also shows the separate feature of a projection 32 on the surface 18 of the needle hub 7 which may be used to deflect the slidable sleeve 5 thereby generating the restoring force. This embodiment provides a highly non-linear return rate since the length of the slidable sleeve 5 is effectively reduced as the slidable sleeve 5 and the needle hub 7 are slid together, thereby increasing the stiffness of the slidable sleeve 5.

The examples above use a chamber and pin, formed as part of the sleeve, to define the different operative positions of the sleeve. It is instead possible to use the cantilever arms 9 themselves to determine the operative positions as well as to provide the restoring force.

FIGS. 9-12 show another embodiment of the present invention which uses tracks to steer the ends of the cantilever arms. Furthermore, this design provides a starting position, an intermediate position in which the needle is partially exposed, an injection position and a safety position.

Thus, the needle hub and the slidable sleeve are adapted to allow the slidable sleeve to be retracted into and held at an intermediate position between the extended position and the retracted position such that, in use, the injection end of the needle 2 projects partially from the slidable sleeve, that is the needle bevel is exposed but the needle is not sufficiently exposed to the extent that the needle may be inserted into the patient. In the intermediate position the locking mechanism is not engaged and hence the slidable sleeve may be retracted further into the (fully) retracted position as it is inserted into the patient. The advantages of this arrangement are that exposing the tip of the needle partially allows the user to position the needle more precisely on, for example, the patient's skin, and also facilitates the aspiration of trapped air and excess drug.

Figure 9:
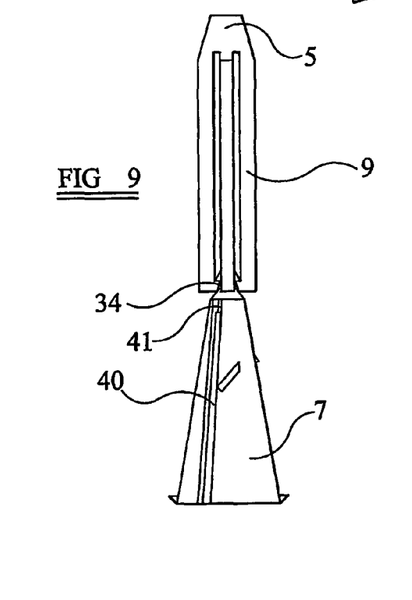
FIGS. 9 and 9a show a second example of safety needle accessory of the invention having an intermediate position.

FIG. 9 shows schematically the safety needle accessory as assembled by the manufacturer. The accessory comprises hub 7, being of conical or other tapering form. Slidable sleeve 5 has cantilever arms 9 attached or more preferably integral thereto, the arms terminating with a projection 33 which engages with an undercut 34 of the hub 7 (shown in more detail in FIG. 9a).

Figure 9A:
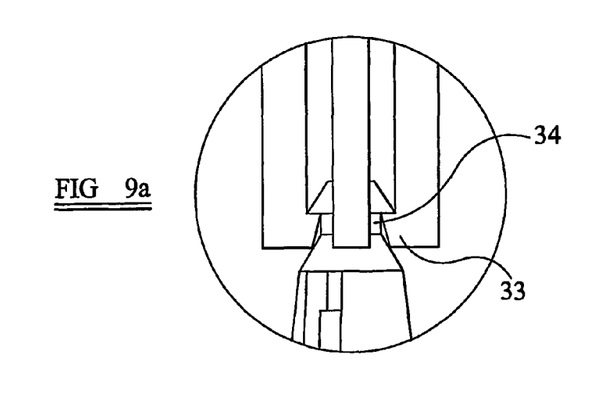

In the position shown in FIG. 9 and FIG. 9a, there is little load on the cantilever arms 9, although sufficient load to hold the components of the safety needle accessory together.

The hub 7 has a track 7a for each cantilever arm which runs the length of the hub. At the top of the track 7a is a recess 7b, and this defines the safety position as will become apparent below. Initially, the sleeve has an angular orientation which means the arms 9 are not aligned with the track 7a.

Figure 10:
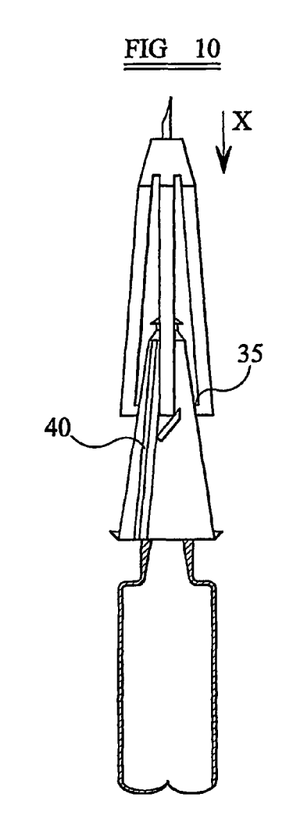
FIG. 10 shows the safety needle of FIGS. 9 and 9a ready to use.

Referring to FIG. 10, in assembling the safety needle 1 to a pre-filled syringe 2, the user will slide slidable sleeve 5 in the direction of the arrow X. In order to facilitate the assembly of the safety syringe, a locking ring or tab 13 (as shown in FIG. 1) may be frangibly connected to the needle hub 7. The sliding of the slidable sleeve 5 causes the cantilever arms 9 to be forced outwards as they move along the surface of the needle hub 7, until at least one of the projections 33 snaps over a catch 35. The cantilever arms 9 are now loaded radially, and exerting a resultant force urging the slidable sleeve 5 into the extended position, but the catch 35 prevents the slidable sleeve 5 from moving in this direction. At this stage the needle is ready for use. The tip of the needle 3 is thus partially exposed, and the user may aspirate any trapped air and excess drug.

Figure 10A:
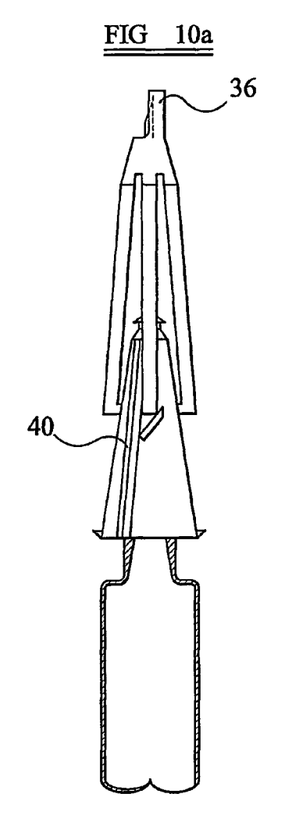
FIG. 10a shows an alternative shroud to increase the protection against needle stick injuries, whilst allowing the needle bevel to be seen immediately prior to giving the injection.

FIG. 10a shows an alternative safety needle accessory in which the safety needle is ready for use, as in FIG. 10, but with an extension 36 on face of the slidable sleeve 5 which only partially shrouds the tip of the needle 3. Such an arrangement will afford more protection, but may make aspiration of air and excess drug slightly more difficult.

Figures 11, 12:
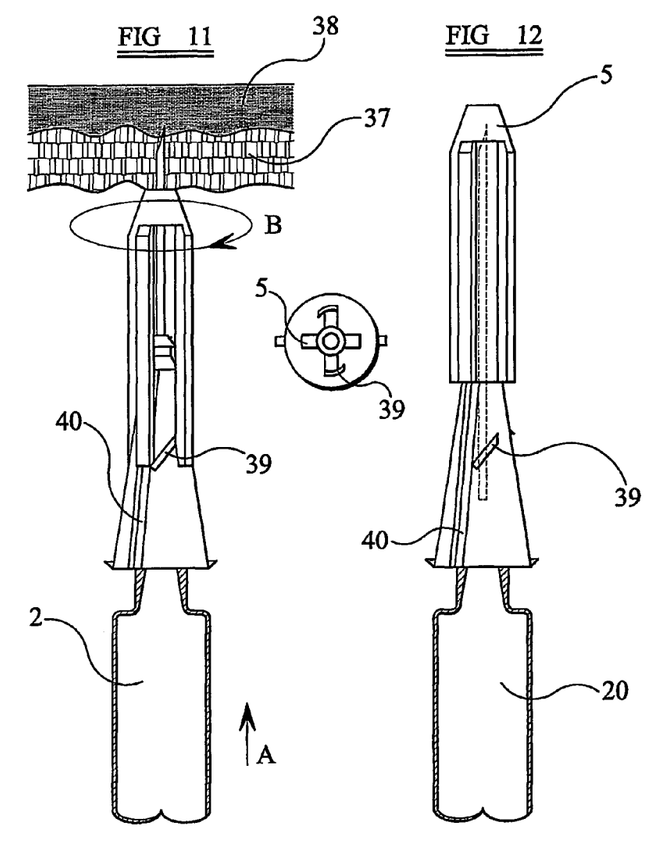
FIG. 11 shows use of the safety needle to inject a medicament.
FIG. 12 shows the safety needle after the injection with the slidable sleeve locked in the extended position.

Referring to FIG. 11, the user pushes the needle 3 in the direction of arrow A through the patient's epidermis 37 and into the subcutaneous tissue 38, which brings the face of the slidable sleeve 5 info contact with the stratum corneum of the patient's epidermis 37. Further movement in the direction of arrow A pushes the slidable sleeve 5 towards the syringe 2, and thus the cantilever arms 9 are forced further outwards by the needle hub 7 which has, of course, been adapted for this purpose. At the same time the end of at least one cantilever arm 5 is forced against a cam 39 which causes the slidable sleeve 5 and cantilever arms 9 to rotate in the direction of arrow B, until the end of cantilever arm 5 which has been forced against the cam 39 drops into the groove 40 forming the track 7a. Groove 40 has a slope towards the needle, which maintains the resultant force of the cantilever arm 5. At this point, (which may represent only a millimeter or two of movement of the slidable sleeve 5), if the safety needle is withdrawn from the patient, the resultant force of the cantilever arms 9 urges the sleeve 5 into the extended position.

Figure 12A:
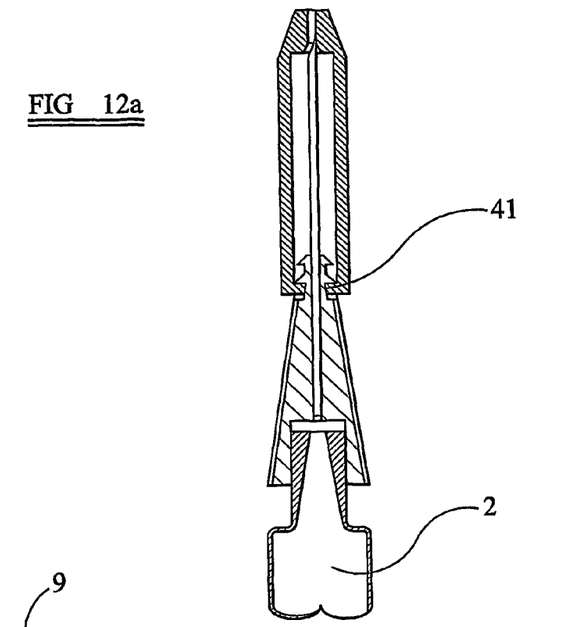
FIG. 12a shows a centre-line section through the safety needle, rotated to show part of the locking mechanism.

At the end of travel towards the safety position, the projections 33 on cantilever arms 5 drop into the hole 41 as shown in FIGS. 12 and 12a. This locks the sleeve 5 in the extended position and prevents the slidable sleeve 5 being pushed back towards the syringe 2, or being pulled off the hub 7. Although the lockably engaging projection 33 and hole 41 are shown with reference to cantilever arms 9, any slidable sleeve 5 may be locked into position using one or more projections and corresponding one or more holes. Such an arrangement results in a less complex, and hence less costly, safety needle accessory and avoids introducing opposing frictional and/or detent forces which result from an integral but independent locking mechanism. An advantage of the projection 33/hole 41 mechanism is that the locking mechanism provides substantially no resistance against the restoring force as the slidable sleeve 5 moves from the retracted position to the extended position. When the slidable sleeve 5 reaches the extended position the locking mechanism engages which then resists the restoring force.

Figure 13:
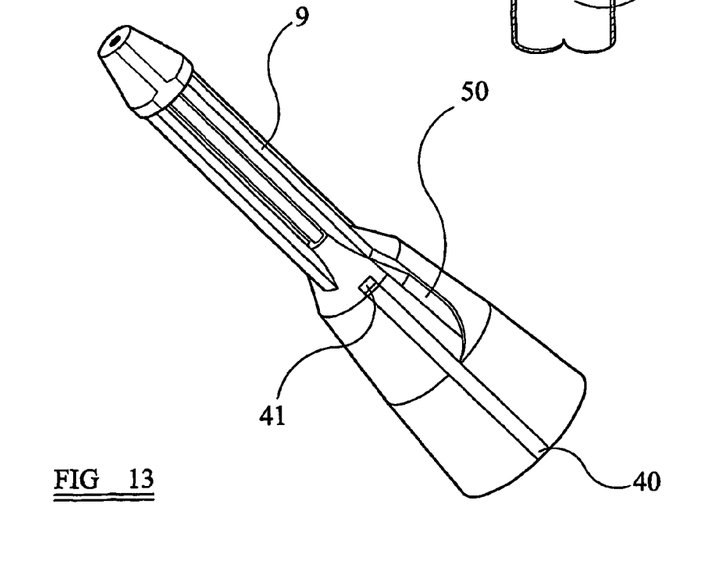
FIG. 13 shows a modification to the hub used in the example of FIG. 12.

In the example above, the angular orientation of the sleeve needs to be correct initially, so that the at least one of the arms 9 follows a path to the latch 35. This can be achieved using a second groove/track 50 as shown in FIG. 13. Initially, at least one of the arms is latched into the top of the track 50, and the track directs the cantilever arm (or another cantilever arm) to the latch 35 (not shown in FIG. 13). The track 50 also then steers the sleeve into the correct angular orientation for the arms 9 to follow the track 40.

In the examples above, the needle is supplied to the user with the needle covered by the sleeve. As mentioned above, it may be desirable to provide an intermediate locked position.

An alternative way to achieve this is to supply the needle to the user in the intermediate position, but with a protective cover. This cover can then engage with the hub, for example the tabs at the base of the hub shown in FIG. 10. The cap is not easily removed until the hub is engaged with the syringe, as only then is there a holding force on the hub, enabling the cap to be removed. Thus, the safety needle can be supplied in an intermediate extended position with a cap, and be treated for medical use with the cap. The cap and needle assembly is then positioned over the syringe, and the cap can then be removed when the needle is to be used.

FIG. 14 shows a design of the hub 7 for this type of operation. A track 40 is again provided, but the starting point for the ends of the cantilever arms is mid-way (or at any other intermediate position) along the track 40, in a branch 52. The branch is designed to hold the cantilever arms in position, and also provides a guide surface to the main track 40, which again causes slight rotation of the sleeve. There is a small step 54 so that once the arms have entered the track, they cannot move back into the branch 52.

The locking of the sleeve in the safety position is also achieved in a different manner. When the sleeve reaches the fully extended position, the arms drop out of the track 40 and engage over a hub/head 56. This means the sleeve can rotate when in the safe position. This is an advantage, as locking the rotation of the sleeve can result in the sleeve deforming when subjected to a lateral force or torque, increasing the possibility of damage or danger.

Figure 14A:
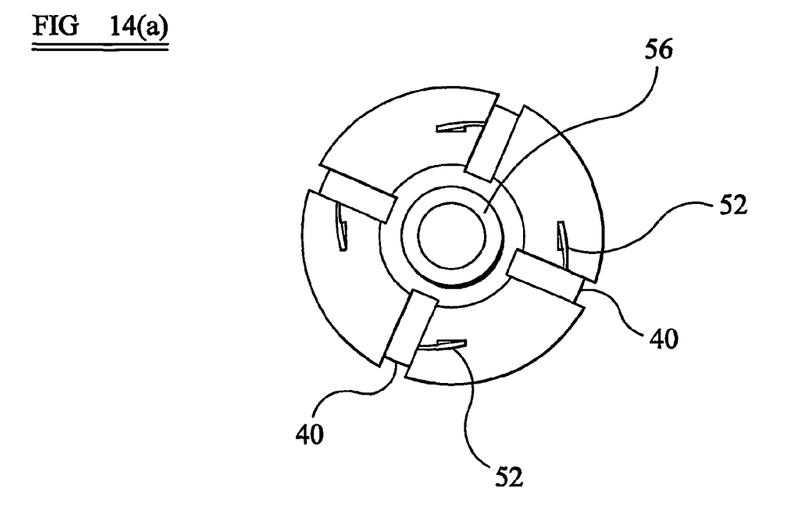
FIGS. 14(a) and (b) show a third example of safety needle hub to form an accessory of the invention.
Figure 14B:
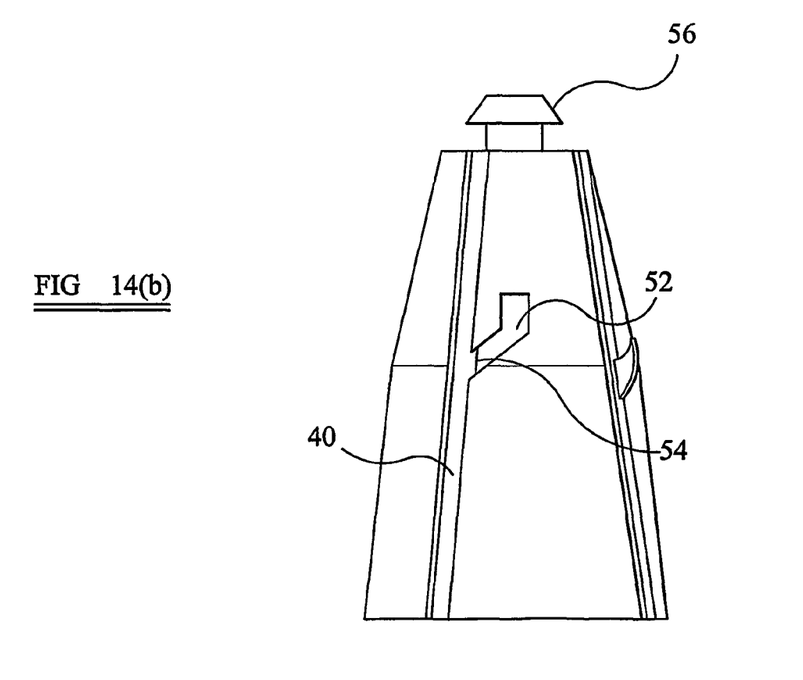

FIG. 14(*a*) shows top view of the hub and FIG. 14(*b*) shows a side view. The same design of sleeve can be used as in other examples.

Figure 15A:
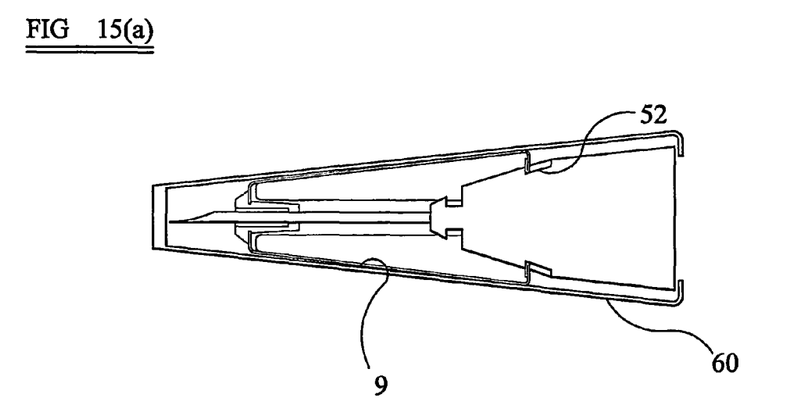
FIGS. 15(a), 15(b) and 15(c) show use of a device having the hub of FIGS. 14(a) and (b)
Figure 15B:
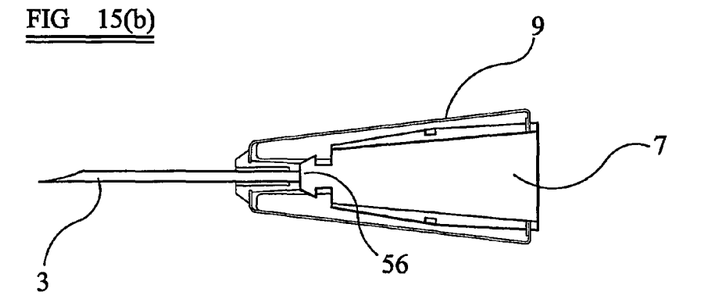
Figure 15C:
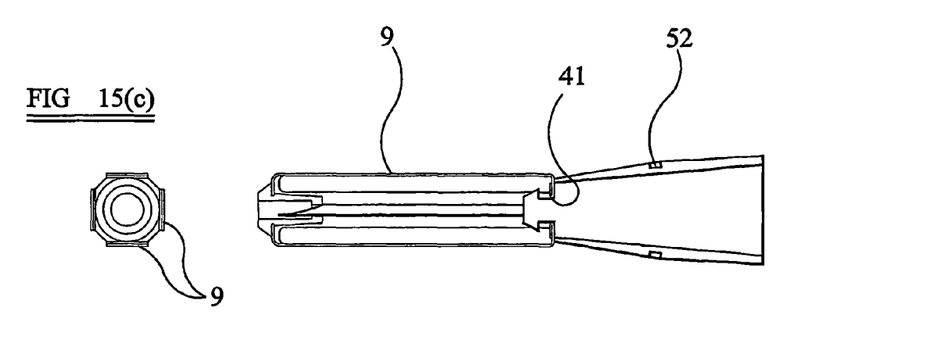

FIG. 15(*a*) shows the starting position, including a cap 60, FIG. 15(*b*) shows the injection position and FIG. 15(*c*) shows the safety position for the design of FIG. 14.

The example of FIGS. 14 and 15 uses a track to guide the sleeve between the injection and safety positions. This prevents any angular rotation of the sleeve during the injection process. As mentioned above, the freedom to rotate can allow forces acting as torques to be absorbed without damage or deformation to the sleeve. Tracks also give a slight frictional resistance when there is contact at their sides.

FIG. 16 is used to explain a design in which the use of tracks is avoided, and the sleeve can rotate during the injection process. It is noted that rotation of the sleeve does not result in rotation of the needle.

FIG. 16(*a*) shows a first design in the starting position, and FIG. 16(*b*) shows the same design in the finishing position, with only two arms 9 shown for clarity. FIGS. 16(*c*) and 16(*d*) show variations to the design.

The hub 7 shown in FIG. 16(*a*) and FIG. 16(*b*) has a smooth conical outer surface. The cantilever arms 9 start off engaged in a small recess 70, and as shown in FIG. 16(*a*), this position of the sleeve gives a short needle projection 72. The assembly is supplied with a cap such as shown in FIG. 15(*a*). FIG. 16(*a*) also shows an enlarged view of the end of an arm in the recess 70.

Figure 16A:
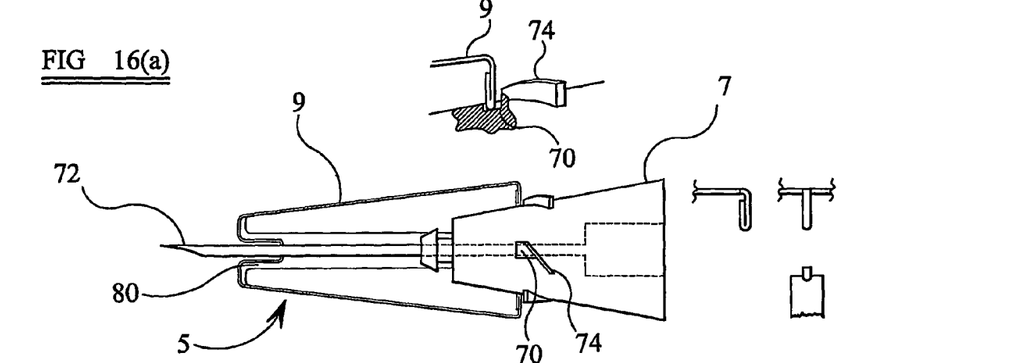
FIGS. 16(a) and 16(b) show a fourth example of accessory of the invention.
Figure 16B:
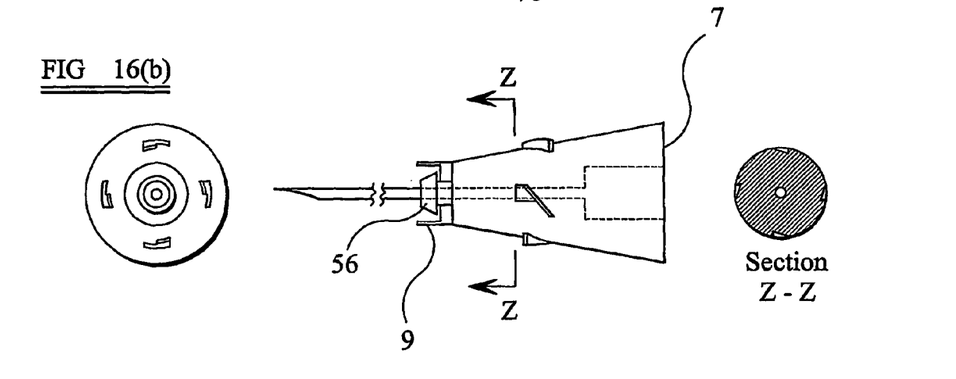
Figure 16C:
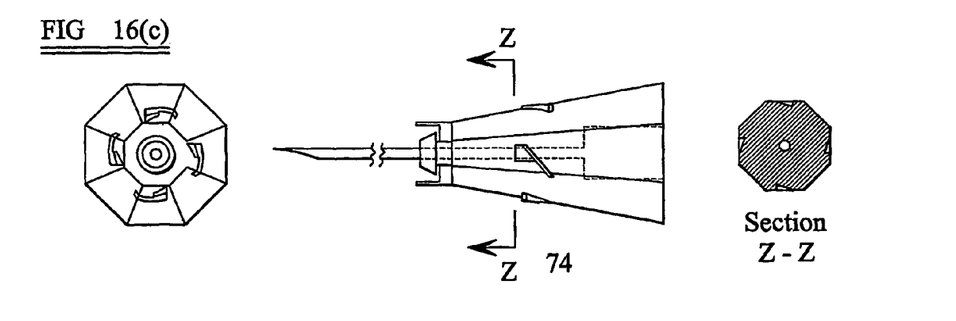
FIGS. 16(c) and 16(d) show modifications to the accessory of FIGS. 16(a) and 16(b).
Figure 16D:
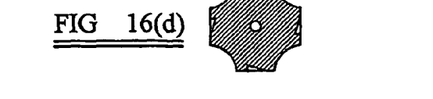

A cam surface 74 deflects the sleeve 5 rotationally as the arms are pushed out of the recess 70. The arms, and therefore the sleeve, can then rotate as the injection takes place. When the sleeve returns towards the safety position of FIG. 16(*b*), the opposite side of the cam surface prevents the arms falling back into the recess 70, so that both sides of the cam 74 providing a guiding function if required.

In the same way as described above, the arms engage over hub/head 56 when in the safety position shown in FIG. 16(*b*).

FIG. 16 shows a modification in which the hub has the shape of a section of an octagonal pyramid. The starting positions for the cantilever arms are in the recesses in one set of faces, and the cams 74 are then designed to push the arms onto adjacent faces. This reduces significantly the chance that the cam surface will be needed when the sleeve returns to the safety position.

As each face of the octagon has the lowest radius in the centre, the arms will be very lightly biased towards the centre. This bias force is much less than the lateral forces which can be encountered when engaging with a track, but further help to reduce the probability that the cam surfaces will be contacted on the return path of the sleeve.

This effect is exaggerated in the design of FIG. 16(*d*) in which the sides of the polygonal cross section are inwardly curved.

Importantly, the cost of the components of the present invention in all embodiments, as well as the assembly costs will be of the same order as those for a conventional needle.

It is preferable that the coefficient of friction between the slidable sleeve 5 and the needle hub 7 is low, so that the resultant biasing force to return the slidable sleeve is not compromised by "stiction", or so high that the force required on the patient's skin to deflect the slidable sleeve 5 is excessive. This may be achieved by careful selection of materials. Such materials are known in the art, for example, the needle hub could be made from a high-density polyethylene or similar drug-compatible plastics material, and the slidable sleeve from an inexpensive plastics material such as polycarbonate, polystyrene, polyester or PVC. A more expensive, highly creep-resistant plastics material, for example polyphenylene sulfone, could also be used.

As an alternative, the slidable sleeve, or just the at least one cantilever arm, may be made from metal, preferably stainless steel. The metal would be fabricated sufficiently thinly to provide the required elastic properties.

The example of FIG. 16 illustrates a pressed metal sleeve 5, and with a deep drawn hub 80. The cost of this component may not exceed the plastics equivalent, and the effects of creep are significantly reduced.

If necessary, a lubricant may be used, or a lubricant may be incorporated with polymers. Generally the materials should be suitable for sterilisation by gamma radiation, but it is possible to select materials compatible with sterilisation by steam or other gas such as ethylene oxide.

In some embodiments, the slidable sleeve, prior to use, is not under any substantial load. Any substantial load indicates a load which is sufficient to cause the material of the slidable sleeve to undergo creepage during storage at ambient temperature.

In the examples where the device is supplied in the intermediate position, there will be a preload. This may make the use of a metal sleeve preferable.

Thus the procedure for using the safety needle is the same as with using conventional needles. Where a locking ring is used, the act of releasing the locking ring is similar to removing the temporarily captive needle cover from a conventional needle. Of course, where a cap is used, this is similar to conventional needle use.

The safety needle 1 may be supplied pre-assembled as shown in FIGS. 1 and 2, and attached by the user to a previously filled syringe 2 by pushing the female Luer 24 of the needle hub 7 onto the male Luer connector 4. The locking ring 13 prevents any displacement of slidable sleeve 5 relative to the needle hub 7. The user releases the locking ring, and may give an injection to the patient by placing the face 6 onto the injection site and pushing on the syringe body in the direction of arrow Y in the normal way of giving an injection. This causes the needle 3 to penetrate the patient's tissue as the slidable sleeve 5 is displaced by the reaction against the patient's skin. The syringe plunger is depressed to dispense the medicament, and the syringe is withdrawn from the patient. The cantilever springs 9 urge the slidable sleeve 5 towards the tip of the needle 3 in the direction of arrow Y, so that the tip of needle 3 is immediately covered. The pawl 20 will have engaged automatically with the face 16 of hub 7 to prevent the slidable sleeve 5 from being pushed back again. The syringe and needle may be disposed of safely without risk of needle stick injury.

In the examples above, the arms are caused to diverge radially as the injection is carried out. Instead, the arms can follow a converging path defined by the hub, and the same elastic restoring force can be generated in this way.

In some examples above the starting point for the sleeve is with a short length of needle exposed. The term "substantially fully surrounding" in respect of the sleeve is intended to cover this configuration in this description and claims.

As an alternative to the tapered outer surface of the needle hub 7, to provide radial expansion/compression of the arms, the slidable sleeve can have at least one cantilever arm which engages a helical track in the outer surface of the needle hub such that, in use, as the needle is inserted into a patient, the at least one cantilever arm is displaced radially by the helical track in the outer surface of the needle hub thereby generating the restoring force. Thus, as the slidable sleeve 5 is caused to move towards the receiving end of the needle hub 7, one or more cantilever arms 9 are forced to follow the direction of the helical tracks. Since the cantilever arms 9 are resilient, a restoring force will be generated.

As an alternative to cantilever arms, the receiving end of the slidable sleeve itself may have elastic properties such that, in use, as the needle is inserted into a patient, the restoring force is generated within the slidable sleeve. Thus, the restoring force can be generated within a radially continuous slidable sleeve, i.e. a sleeve without cantilever arms. The elastic properties may be achieved by using an elastic material, such as an elastomeric polymer. Alternatively, the receiving end of the slidable sleeve may be concertinaed, with the ridges, of course, running parallel to the hollow needle. The elastic properties could also be generated using a circumambient spring attached to the slidable sleeve.

As previously mentioned hereinabove, the syringe may be supplied empty or pre-filled. When a pre-filled syringe is used, the syringe is preferably sealed using a sealing cap or plug to prevent evaporation or loss of the drug, excipient, carrier and/or diluent by, for example, thermal expansion.

As well as application to a syringe, the same safety needle accessory described herein could form the basis of a intravenous giving set, so that the insertion of the needle into the patient's vein is simple and safe. Indeed, the safety needle accessory of the present invention may be used with any suitable injection device.

Other modifications of the present invention will be apparent to those skilled in the art.

The invention claimed is:

1. A safety needle attachment for surrounding a needle having a longitudinal axis, comprising:
   a hub;
   a sleeve surrounding the hub and slidable along the hub in the axial direction;
   wherein the sleeve has a radially elastically deformable portion, and the hub has a radially converging or diverging portion, and
   wherein the sleeve is slidable in a first axial direction between a first position for fully or substantially fully surrounding the needle with the sleeve, and a second position for exposing the needle, wherein the converging or diverging portion of the hub causes elastic radial deformation of the deformable portion as the sleeve slides between the first and second positions, and wherein the sleeve is further slidable in a second, opposite, axial direction between the second position and a third position for fully surrounding the needle by the sleeve, the force for sliding between the second and third positions being provided by the stored elastic energy in the radially deformable portion.

2. An attachment as claimed in claim 1, wherein the portion of the sleeve is elastically deformable radially outwardly, and the hub has a radially diverging portion.

3. An attachment as claimed in claim 1, wherein the third position of the sleeve is further towards the injection end of the needle than the first position.

4. An attachment as claimed in claim 3, wherein a latching arrangement engages when the sleeve reaches the third position to prevent subsequent movement of the sleeve in the first axial direction.

5. An attachment as claimed in claim 4, wherein the latching arrangement comprises a tab of the sleeve which engages with an end face of the hub.

6. An attachment as claimed in claim 3, further comprising a mechanism for initially limiting movement of the sleeve in the second axial direction when the sleeve is in the first position.

7. An attachment as claimed in claim 6, wherein the mechanism releases after initial movement in the first axial direction, and thereafter permits the sleeve to move in the second axial direction to the third position.

8. An attachment as claimed in claim 6, wherein the mechanism comprises a radially extending pin of the sleeve which is held in a first position, and a pawl of the hub which is tripped by the pin upon initial movement of the sleeve in the first axial direction.

9. An attachment as claimed in claim 1, wherein an intermediate position is provided between the first and second positions of the sleeve, in which the sleeve is retained in position.

10. An attachment as claimed in claim 9, wherein the injection end of the needle projects partially from the sleeve in the intermediate position.

11. An attachment as claimed in claim 1, wherein the third position of the sleeve is the same axially as the first position.

12. An attachment as claimed in claim 11, wherein movement of the sleeve in the first axial direction causes rotation of the sleeve about the longitudinal axis.

13. An attachment as claimed in claim 12, wherein an intermediate position is provided between the first and second positions of the sleeve, in which the sleeve is retained in position.

14. An attachment as claimed in claim 13, wherein the injection end of the needle projects partially from the sleeve in the intermediate position.

15. An attachment as claimed in claim 13, wherein the sleeve is held in the intermediate position by engagement of the deformable portion of the sleeve over a tab of the hub.

16. An attachment as claimed in claim 15, wherein the rotation of the sleeve about the longitudinal axis is such that the deformable portion does not engage the tab of the hub when the sleeve moves from the second to the third positions.

17. An attachment as claimed in claim 1, wherein the radially converging or diverging portion of the hub comprises at least one recess for engaging with the deformable portion of the sleeve in a starting position of the sleeve, and otherwise has a substantially smooth outer surface.

18. An attachment as claimed in claim 17, wherein the smooth outer surface is conical.

19. An attachment as claimed in claim 17, wherein the smooth outer surface is polygonal in cross section perpendicular to the longitudinal axis.

20. An attachment as claimed in claim 17, wherein the starting position of the sleeve causes the needle to project from the sleeve, and wherein the attachment further comprises a cap.

21. An attachment as claimed in claim 17, wherein the hub further comprises a head, and wherein the deformable portion engages under the head in the third position of the sleeve.

22. An attachment as claimed in claim 1, wherein the radially converging or diverging portion of the hub comprises at least one track running the length of the hub, and a branch to the track which defines a recess for engaging with the deformable portion of the sleeve in a starting position of the sleeve.

23. An attachment as claimed in claim 22, wherein the starting position of the sleeve causes the needle to project from the sleeve, and wherein the attachment further comprises a cap.

24. An attachment as claimed in claim 22, wherein the hub further comprises a head, and wherein the deformable portion leaves the track in the third position of the sleeve and engages under the head.

25. An attachment as claimed in claim 1, wherein the deformable portion of the sleeve comprises a plurality of circumferentially spaced tines.

26. An attachment as claimed in claim 1, wherein the vessel for containing a medicament comprises a syringe.

27. An attachment as claimed in claim 1, further comprising a removable locking ring connected to the hub and/or the sleeve for preventing movement of the sleeve relative to the hub.

28. An attachment as claimed in claim 27, wherein the removable locking ring is frangibly connected to the needle hub and/or the sleeve.

29. An attachment as claimed in claim 1, wherein the sleeve is, prior to use, not under any substantial load.

30. An attachment as claimed in claim 1, wherein an end of the hub is adapted for connection to a Luer connector.

31. An attachment as claimed in claim 1, wherein the radially converging or diverging portion comprises a frusto-conical surface.

32. An attachment as claimed in claim 1, wherein the elastic properties of the deformable portion of the sleeve are provided by a circumambient spring.

33. A safety needle attachment for surrounding a needle having a longitudinal axis, comprising:
   a hub having a radially converging or diverging portion;
   a sleeve having at least one cantilever arm, the sleeve configured to slide along the hub in an axial direction,
   wherein the sleeve is slidable in a first axial direction between a first position for fully or substantially fully surrounding the needle with the sleeve, and a second position for exposing the needle,
   wherein the at least one cantilever arm radially deforms upon sliding on the converging or diverging portion of the hub between the first and second positions, and
   wherein the sleeve is further slidable in a second, opposite, axial direction between the second position and a third position for fully surrounding the needle by the sleeve; and
   a restoring force generated by the radial deformation of the at least one cantilever arm for sliding the sleeve between the second and third positions.

34. A safety needle attachment for surrounding a needle having a longitudinal axis, comprising:
   a hub having a radially converging or diverging portion;
   a sleeve having:
      a deformable portion, and
      a circumambient spring operatively connected to the sleeve to elastically deform the deformable portion, the sleeve configured to slide along the hub in an axial direction,
   wherein the sleeve is slidable in a first axial direction between a first position for fully or substantially fully surrounding the needle with the sleeve, and a second position for exposing the needle,
   wherein the deformable portion radially deforms upon sliding on the converging or diverging portion of the hub between the first and second positions, and
   wherein the sleeve is further slidable in a second, opposite, axial direction between the second position and a third position for fully surrounding the needle by the sleeve; and
   a restoring force generated by the radial deformation of the deformable portion for sliding the sleeve between the second and third positions.

* * * * *